(12) United States Patent
Goia

(10) Patent No.: US 11,453,058 B2
(45) Date of Patent: Sep. 27, 2022

(54) PREPARATION OF HIGHLY STABLE CONCENTRATED DISPERSIONS OF SILVER NANOPARTICLES USING SYNERGISTIC DISPERSING AGENTS

(71) Applicant: NOBEL /NOBLE ELEMENTS/ LLC, Cheyenne, WY (US)

(72) Inventor: Dan Goia, Flemington, NJ (US)

(73) Assignee: NOBEL /NOBLE ELEMENTS/ LLC, Cheyenne, WY (US)

( * ) Notice: Subject to any disclaimer, the term of this patent is extended or adjusted under 35 U.S.C. 154(b) by 71 days.

(21) Appl. No.: 16/879,697

(22) Filed: May 20, 2020

(65) Prior Publication Data

US 2021/0299750 A1 Sep. 30, 2021

Related U.S. Application Data

(60) Provisional application No. 63/001,127, filed on Mar. 27, 2020.

(51) Int. Cl.
*B22F 9/24* (2006.01)
*A61K 33/38* (2006.01)
*B01J 13/00* (2006.01)
*A61K 9/10* (2006.01)

(52) U.S. Cl.
CPC ............... *B22F 9/24* (2013.01); *A61K 9/10* (2013.01); *A61K 33/38* (2013.01); *B01J 13/0043* (2013.01); *B22F 2301/255* (2013.01); *B22F 2304/054* (2013.01)

(58) Field of Classification Search
CPC ............... B22F 9/24; B22F 2301/255; B22F 2304/054; B22F 2999/00; A61K 9/10; A61K 33/38; A61K 9/5161; B01J 13/0043; B01J 13/0013
See application file for complete search history.

(56) References Cited

U.S. PATENT DOCUMENTS 7,842,274 B2 * 11/2010 Goia .................. B22F 1/052
423/604

OTHER PUBLICATIONS

Natsuki et al, A Review of Silver Nanoparticles: Synthesis Methods, Properties and Applications, International Journal or Materials Science and Applications, 4(5): pp. 325-332 (Year: 2015).*
Balantrapu et al., Silver nanoparticles for printable electronics and biological applications, Journal of Materials Research 24, 2828-2836 (2009). https://doi.org/10.1557/jmr.2009.0336.
(Continued)

*Primary Examiner* — Carlos A Azpuru
(74) *Attorney, Agent, or Firm* — Procopio, Cory, Hargreaves & Savitch LLP

(57) ABSTRACT

Methods for preparing highly stable concentrated dispersions of silver nanoparticles and described herein. Contemplated methods comprise combining a selected polysaccharidic dispersant with a selected non-reacting dispersant to yield concentrated silver dispersions with enhanced stability and lowered undesirable residual organics. Contemplated methods further comprise selecting an appropriate source of silver ions to reduce the ionic strength of the reaction medium and final silver dispersions.

20 Claims, 2 Drawing Sheets

(56) References Cited

OTHER PUBLICATIONS

Paciotti et al., Colloidal Gold: A Novel Nanoparticle Vector for Tumor Directed Drug Delivery, Drug Delivery, ISSN: 1071-7544 (Print) 1521-0464 (Online) Journal homepage: https://www.tandfonline.com/loi/idrd20, 11:169-183, 2004.

Dan V. Goia, Preparation and formation mechanisms of uniform metallic particles in homogeneous solutions, Journal of Materials Chemistry, 14, (2004) pp. 451-458, DOI: 10.1039/b311076a.

Hardonk et al., Zonal heterogeneity of rat hepatocytes in the in vivo uptake of 17 nm colloidal gold granules, Histochemistry, vol. 83, (1985) pp. 473-477, 10.1007/BF00509211.

Renaud et al., Hepatic Metabolism of Colloidal Gold-Low-Density Lipoprotein Complexes in the Rat: Evidence for Bulk Excretion of Lysosomal Contents into Bile, Hepatology, vol. 9, No. 3, (1989) pp. 380-392.

Sau et al., Biomedical Applications of Gold Nanoparticles, Fine Particles in Medicine and Pharmacy, Ed. Egon Matijević, Springer, New York, 2011, DOI 10.1007/978-1-4614-0379-1, pp. 101-145.

\* cited by examiner

PREPARATION OF HIGHLY STABLE CONCENTRATED DISPERSIONS OF SILVER NANOPARTICLES USING SYNERGISTIC DISPERSING AGENTS

CROSS-REFERENCE TO RELATED APPLICATIONS

This application claims priority to U.S. provisional patent application with Ser. No. 63/001,127, which was filed Mar. 27, 2020. This and all other extrinsic materials discussed herein are incorporated by reference in their entirety. Where a definition or use of a term in an incorporated reference is inconsistent or contrary to the definition of that term provided herein, the definition of that term provided herein applies and the definition of the term in the reference does not apply.

FIELD OF THE INVENTION

The field of the invention is silver nanoparticle dispersions and methods of preparing silver nanoparticle dispersions.

BACKGROUND

Silver nanoparticles have unique properties that make them suitable for incorporation into a growing number of products ranging from biological and chemical sensors, conductive inks, pastes and filler. Silver nanoparticles are also used in antimicrobial coatings, biomedical devices, photonic devices and molecular diagnostics.

In the preparation of silver nanoparticles, polymeric dispersants are effective additives for preventing particles aggregation in liquid media. While very dilute silver sols (<0.01 mol/L Ag) can be prepared in absence of dispersants, in concentrated systems they are necessary to prevent the particles aggregation due to the high ionic strength.

The outstanding effectiveness of polymeric extracts obtained from plants ('gums') and animals (gelatin) for certain uses has been widely exploited since antiquity and validated by many recent systematic scientific studies. Having a high solubility in water, polymeric extracts obtained from plants and animals are excellent choices for preparing a wide variety of aqueous colloidal systems including silver sols. Their outstanding 'colloid protective' capacity is primarily due to their large molecules, which are more effective in screening the interparticles attractive forces (primarily Van der Waals).

In general, dispersing agents are used strictly as 'protective colloids' in combination with dedicated reducing agents capable of reducing silver ions/salts (glucose, hydrazine, ascorbic acid, hydroxylamine, etc.). As polymeric polysaccharides incorporate sugar moieties in their molecule, they have reducing properties as well. Indeed, in selected reaction conditions it was shown that polymeric polysaccharides can yield certain stable dispersions of silver nanoparticles in absence of a dedicated reductant. See Goia et al., U.S. Pat. No. 7,842,274; Goia D. V., Balantrapu, K., Journal of Materials Research 24, 9 (2009) 2828-2836.

U.S. Pat. No. 7,842,274 teaches preparation of silver-based particles and electrical contact materials. The silver nanoparticles were prepared by adding an $AgNO_3$ solution and a NaOH solution under strong agitation in a reaction vessel containing an aqueous solution of a polysaccharide. An Ag(+1)-oxide species was generated, and the temperature was raised and suspension stirred for 45 minutes. The resulting silver nanoparticles were separated from the mother liquor and washed with DI water and ethanol. The particles were dried overnight and screened through a mesh screen. Silver nanoparticles prepared using the methods of the '274 patent were noted as having a medium silver particle size (TEM) of d50=20 nm, and a maximum particle size of d100=60 nm.

However, the inherent structural change in the polysaccharide macromolecule following the loss of electrons tends to diminish their dispersing efficiency. Consequently, a large excess of polysaccharide must be added in the system to ensure the presence of sufficient unaltered polymer macromolecules capable of preventing particles aggregation. The excess residual dispersant causes significant problems during the processing of silver nanoparticles and potential adverse effects in many applications. Further, silver nanoparticles prepared in connection with the '274 patent yield relatively large silver nanoparticles, which are undesirable from a toxicity perspective when used in drug delivery.

The present disclosure is directed toward one or more improved features identified below, and to methods and preparations that address the above-mentioned problems.

SUMMARY OF THE INVENTION

The present invention is directed to a method of producing a highly stable, concentrated dispersion of silver nanoparticles. The method comprises dissolving a combination of a reducing dispersant and a co-dispersant in deionized water to form a first solution, and combining the first solution with at least one of a silver compound and a first mixture prepared by adding a silver compound to deionized water. The method further comprises mixing the slurry with a basic solution to form an alkaline basic slurry, and heating the alkaline basic slurry to yield highly uniform silver nanoparticles. In some preferred aspects, the highly uniform silver nanoparticles are all less than or equal to 25 nanometers (nm) in size, or all less than or equal to 15 nm in size. In some preferred aspects, the highly uniform silver nanoparticles are all between 5-25 nm in size, all between 5-15 nm in size, or all about 10 nm. As used herein, the term "about" or "substantially" should be interpreted broadly to mean within 10%.

The present invention is also directed to highly stable concentrated dispersions of silver nanoparticles. The highly stable concentrated dispersions can be prepared using a method as set forth herein. In some preferred aspects, the silver nanoparticles of the highly stable concentrated dispersion are all less than or equal to 25 nanometers (nm) in size, or all less than or equal to 15 nm in size. In some preferred aspects, the highly uniform silver nanoparticles are all between 5-25 nm in size, all between 5-15 nm in size, or all about 10 nm.

Contemplated uses for the silver nanoparticles and/or the highly stable concentrated dispersions of silver nanoparticles include, among other things, use as antimicrobial, antiviral, anti-inflammatory, and anti-cancer agents, use as medical device coatings, optical sensors, and cosmetics.

Various objects, features, aspects and advantages of the present invention will become more apparent from the following detailed description of preferred embodiments of the invention.

BRIEF DESCRIPTION OF THE DRAWINGS

The details of embodiments of the present disclosure can be gleaned in part by study of the accompanying drawings, in which like reference numerals refer to like parts, and in which.

DETAILED DESCRIPTION

Figure 1:
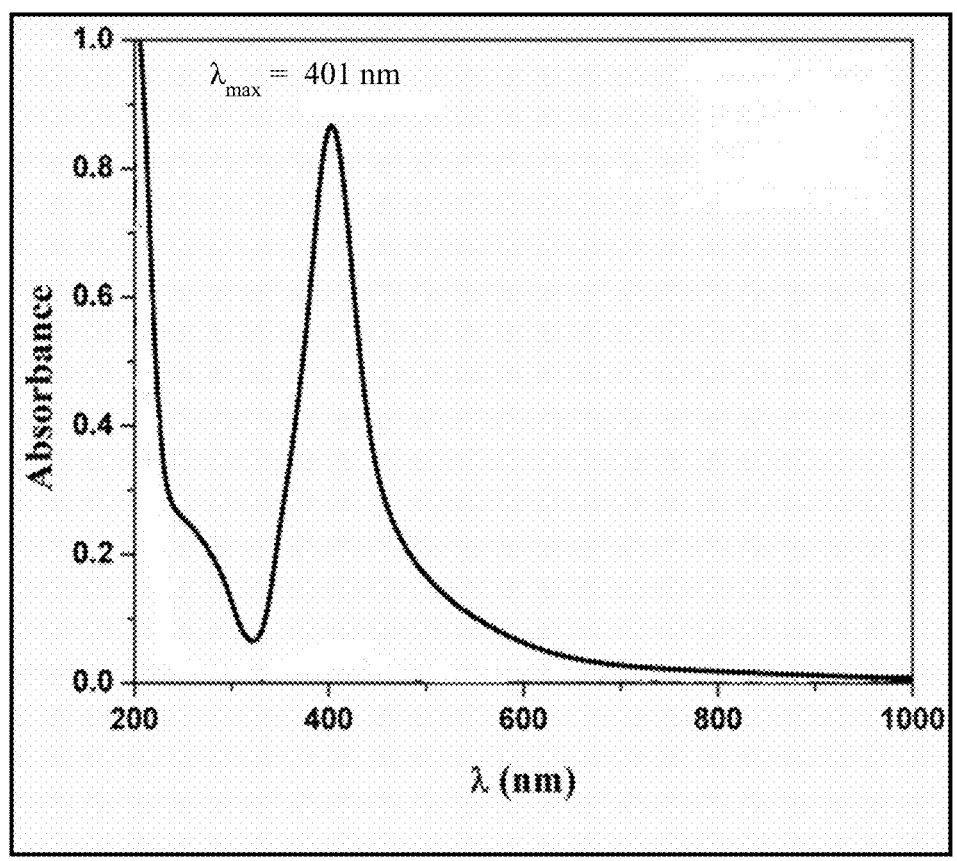
FIG. 1 is a UV-Vis of a dilute aliquot obtained by diluting the dispersion of Example 1 100 times.

The inventor has discovered methods of producing a highly stable, concentrated dispersion of silver nanoparticles in which at least 80%, at least 85%, at least 90%, at least 95%, at least 99% or even 100% of the silver nanoparticles are under 100 nm, more preferably under 75 nm, more preferably under 50 nm, and even more preferably under 25 nm. Highly stable concentrated dispersions of silver nanoparticles, for example, those prepared using the methods described herein, are described.

The method comprises dissolving a combination of a reducing dispersant and a non-reactive co-dispersant in deionized water to form a first solution, and combining the first solution with at least one of a silver compound and a first mixture prepared by adding a silver compound to deionized water. The method further comprises mixing the slurry with a basic solution to form an alkaline basic slurry, and heating the alkaline basic slurry to yield highly uniform silver nanoparticles.

The silver compound may comprise any suitable silver compounds useful to produce silver nanoparticles. A preferred silver compound for the methods and dispersions described herein is silver oxide. An inventive element of the inventive subject matter is the reduction of the ionic strength of the reaction medium and final silver dispersion by selecting an appropriate source of silver ions, for example, a silver oxide.

It should be appreciated that most precipitation processes start from silver nitrate as it is the most accessible, inexpensive, and convenient to work with. In the precipitation of concentrated silver sols, however, the nitrate ions inevitably generate a high ionic strength. As a result, a larger amount of dispersant is needed to prevent particle aggregation. To mitigate the negative effect of the ionic strength on colloidal stability, Applicant selected, as an example, purified silver oxide as a starting salt in the precipitation process. Since the nitrate ions are completely eliminated during the purification of the oxide, the system's ionic strength is drastically decreased and a smaller amount of dispersant is required to provide colloid stability.

Another inventive element of the inventive subject matter is using a reducing dispersant capable of effectively reducing silver ions with a non-reacting dispersant that is highly effective at very low concentrations. The approach advantageously yields concentrated silver dispersions with enhanced stability while significantly lowering the amount of undesirable residual organics by eliminating the need for a large excess of reducing dispersant. Without wishing to be bound by any particular theory, it is believed that the use of a polysaccharide dispersant such as Arabic gum with a non-reacting dispersant such as sodium alginate as described herein has a synergistic effect. For example, the combination may enhance the protective colloid ability of the non-reacting dispersant and/or reducing capabilities of reducing dispersant at lower amounts when compared to those components on their own.

The criteria for selecting the reducing dispersant (e.g., a reducing polysaccharide) may include the following. First, it should be capable of reducing completely the silver ions/salt for obvious practical and economic reasons. Secondly, the polysaccharide should reduce rapidly the silver ions to ensure the fast nucleation needed to obtain small and uniform silver nanoparticles. Some selection criteria for reducing dispersants may be found in Goia, D. V., *Journal of Materials Chemistry*, 14, (2004) 451-458.

Arabic gum was shown to be capable of reducing silver ions and rapidly reducing silver ions to ensure the fast nucleation needed to obtain small and uniform silver nanoparticles, and is a suitable reducing dispersant. Other natural 'gums' (e.g., tragacanth) have similar structural features and in suitable conditions are also effective and contemplated herein, among other dispersants.

One criterion in selecting the second dispersant to be provided in smaller amounts may be its ability to provide, at lower concentrations, similar or better protective colloid efficiency than the reducing dispersant. In general, the stabilizing action improves with increasing dispersion viscosity. The salts of alginic acid belong to a class of macromolecular compounds known as viscosity builders. They create very viscous aqueous solutions and can even form hydrogels in certain conditions. Due to its swelling properties, sodium alginate may be a preferred co-dispersant as it provides better colloid stabilizing efficiency at concentrations 10 to 15 times lower than Arabic gum. Other non-reducing water soluble substances from this viscosity builders category, for example those that provide better colloid stabilizing efficiency at concentrations 5-20 or 10-15 times lower than the polysaccharide dispersant, should be considered covered by the present disclosure, among other dispersants.

Another potential criterion in selecting the co-dispersant relates to its potential ability to alter the properties of the silver surface. Since the co-dispersant remains structurally unaffected during the reduction, it can be used to predictably modify the surface of the silver through spontaneous physical or chemical attachment. Although the suitability of the co-dispersant to provide the desired surface properties (charge, functionality, etc.) for a specific application should be evaluated separately, the concept embodied in this application remains the basis for such future discoveries.

In some contemplated aspects, the co-dispersant may be present at a concentration of less than 1/8 a concentration of the reducing dispersant. Additionally or alternatively, the amount of the silver compound added to the first solution (directly or with deionized water as a first mixture) can be between 1.8-3 times an amount of the combination of the reducing dispersant and co-dispersant dissolved in water. Where a first mixture of the silver compound is added to the first solution, the volume of the first mixture can be between, for example, 1.5-2.5 the volume of the first solution.

The basic solution added to form an alkaline basic slurry that is heated to yield highly uniform silver nanoparticles can comprise, for example, sodium hydroxide (NaOH).

Below is an example of preparing highly stable concentrated dispersions of silver nanoparticles in accordance with a method of the inventive subject matter.

Example 1

24.6 g of freshly precipitated and thoroughly washed $Ag_2O$ (equivalent of 23.0 g Ag metal) are added to 200 mL deionized water in a 500 mL glass beaker. Separately, 11.6 g Arabic gum (reducing dispersant) and 0.4 g sodium alginate (co-dispersant) are dissolved in 100 mL DI water for at least one hour. The dispersant solution is added to the silver oxide and the slurry is subjected for at least 20 more minutes to high shear mixing using a Dispermat-type device while ensuring the temperature does not exceed 50° C. Using 50 mL DI water, the content of the beaker is transferred quantitatively into a 2.0 L glass reactor provided with a three-blade propeller connected to a variable speed motor and heating capabilities. After adding 12.5 mL NaOH 10N and adjusting the volume of the slurry to 1.0 L with DI water, under vigorous mixing the temperature of the dispersion is brought rapidly (over 20 minutes) to 65° C. where is maintained for 30 minutes to convert the silver oxide to silver nanoparticles. The resulting silver dispersion contains 2.3% Ag. For electron microscopy analysis the Ag nanoparticles can be isolated by ultracentrifugation. The UV-Vis analysis can be performed by diluting the final dispersion 100 times.

Product Data

FIG. 1 is a UV-Vis of a dilute aliquot obtained by diluting the dispersion of Example 1 100 times. The dark brown silver dispersion contains highly dispersed silver nanoparticles as testified by the plasmon band recorded by the UV-Vis analysis. The narrow peak suggests the presence of highly uniform nanoparticles while the low background absorption (over 600 nm) indicates the absence of large silver entities. The stability of the dispersion was excellent as indicated by the lack of particles settling and changes in the UV-Vis spectrum after 360 days.

Figure 2A:
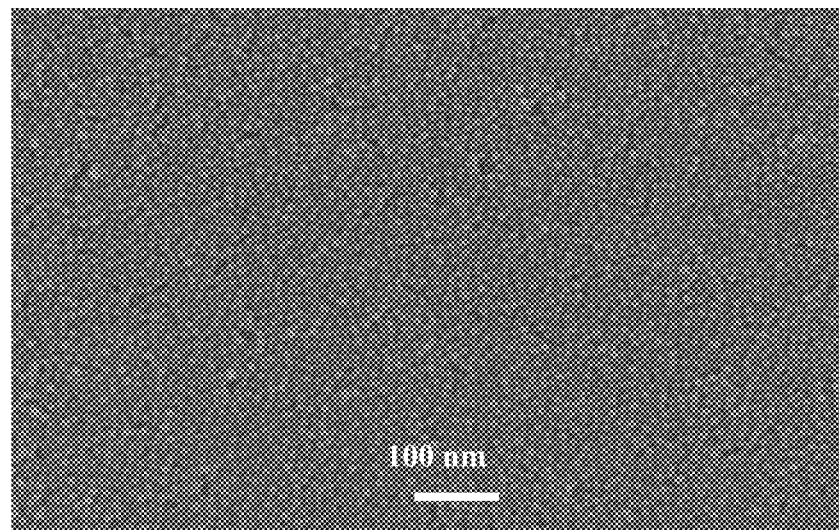
FIG. 2A shows a FESEM image of prepared Ag nanoparticles according to Example 1.
Figure 2B:
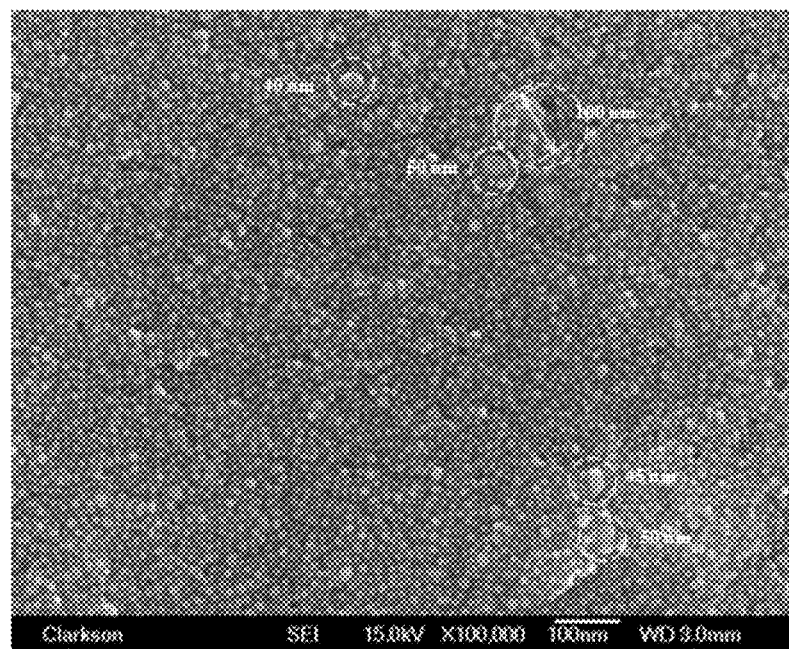
FIG. 2B shows a SEM with large particles obtained from a sample generated in the conditions in U.S. Pat. No. 7,842,274.

FIGS. 2A-2B show FESEM images of prepared Ag nanoparticles from present disclosure, Example 1 (FIG. 2A), and SEM with large particles obtained from a sample generated in the conditions in U.S. Pat. No. 7,842,274 (FIG. 2B).

The FESEM images (e.g., image shown in FIG. 2A) showed the presence of uniform nanoparticles with an average size of ~10 nm and the absence of larger particles or aggregates. As can be seen in comparing FIG. 2A to FIG. 2B, there is a substantial improvement in particle uniformity that was detected even though the specific consumption of reducing dispersant (g or Arabic gum per g silver) has been reduced by about 50% and replaced by a much smaller amount of the second, non-reacting dispersant.

Viewed from another perspective, even though a substantial amount of Arabic gum (e.g., 11.6 g instead of about 19-20 g) was replaced with only 0.4 g of the co-dispersant alginate, a noticeable improvement is seen while reducing the overall amount of undesirable residual organics at the same time. Viewed from yet another perspective, the use of two dispersants as described herein can result in a reduction in the total amount of dispersant used (e.g., by between 25-60%, between 30-55%, between 35-45%) while showing greater or equal dispersion, stability, and/or uniformity.

The difference is particles uniformity is pronounced. The single dispersant procedure allow large particles (up to 40-50 nm or even larger) to form, as shown in FIG. 2B. In FIG. 2A, all of the silver nanoparticles are less than 25 nm in size (e.g., within 200% of 10 nm; about 10 nm).

Where the inventive subject matter is used in, for example, antimicrobial or antiviral applications, the two dispersants approach yielding highly uniform Ag particles around 10 nm (with no particles larger than 15 nm) is advantageous since there is information in the literature showing that, when used as a drug delivery vector, gold particles/aggregates larger than 40 nm are accumulated in internal organs and become toxic (in the case of silver the toxicity would likely manifest as argyria). If this holds true, the silver colloidal of the inventive subject matter would be less prone to cause argyria. Further, there is information in the literature showing that only small particles (i.e., nonaggregated 33 nm or less) are cleared from the body. Although the fate of colloidal gold particles was not evaluated in the current studies, several preclinical models suggest that the electrostatically stabilized particles are taken up by hepatocytes (Hardonk et al. 1985; Renaud et al. 1989), not Kupffer cells, excreted into the bile and expelled from the body in feces. Two key factors influence the clearance of gold particles. First, smaller colloidal gold particles stabilized with either a protein or a polymer were preferentially taken up by the hepatocytes and ultimately excreted into the bile and eliminated in the feces. See Id. Secondly, blocking Kupffer cell activity with gadolinium chloride also increased the fraction of particles cleared by the hepatocytes. See Renaud et al. 1989. The size and RES-avoiding properties of PT-cAu-TNF vector support similar mechanisms for clearance of the particles.

OTHER EXAMPLES

It is contemplated that methods in accordance with the following may be used to prepare silver nanoparticle dispersions of the inventive subject matter. About 24.6 g of freshly precipitated and thoroughly washed $Ag_2O$ (equivalent of about 23.0 g Ag metal) may be added to about 200 mL deionized water in a 500 mL glass beaker. Separately, about 11.6 g Arabic gum (reducing dispersant) and about 0.4 g sodium alginate (co-dispersant) may be dissolved in 100 mL DI water for any suitable amount of time, for example, at least one hour. The dispersant solution may be added to the silver oxide and the slurry may be subjected for about 20-40 minutes (or longer) to high shear mixing using a Dispermat-type device while ensuring the temperature does not exceed about 50° C. Using about 50 mL DI water, the content of the beaker is transferred quantitatively into a 2.0 L glass reactor provided with a three-blade propeller connected to a variable speed motor and heating capabilities. After adding about 12.5 mL NaOH 10N and adjusting the volume of the slurry to about 1.0 L with DI water, under vigorous mixing the temperature of the dispersion is brought rapidly (over about 20-40 minutes minutes) to about 65° C. where is maintained for about 30 minutes to convert the silver oxide to silver nanoparticles. The resulting silver dispersion may contain about 2.3% Ag. For electron microscopy analysis the Ag nanoparticles can be isolated by ultracentrifugation. The UV-Vis analysis can be performed by diluting the final dispersion, for example, about 100 times.

It is also contemplated that methods in accordance with the following may be used to prepare silver nanoparticle dispersions of the inventive subject matter. About 20-29.2 g of freshly precipitated and thoroughly washed $Ag_2O$ may be added to deionized water. Separately, about 8-15.2 g Arabic gum (reducing dispersant) and about 0.1-1 g sodium alginate (co-dispersant) may be dissolved in DI water for any suitable amount of time, for example, about an hour or at least one hour. The dispersant solution may be added to the silver oxide and the slurry may be subjected for about 20-40 minutes (or any suitable amount of time) to high shear mixing using a Dispermat-type device while ensuring the temperature does not exceed about 60° C., or more preferably about 50° C. Using DI water, the content of the beaker is transferred into a glass reactor provided with a three-blade propeller connected to a variable speed motor and heating capabilities. After adding about 9-16 mL NaOH solution and adjusting the volume of the slurry to about 0.5-1.5 L, about 1.0 L (or any other suitable volume) with DI water, under vigorous mixing the temperature of the dispersion is brought rapidly to about 65 or between 55-75° C. where is maintained to convert the silver oxide to silver nanoparticles. The resulting silver dispersion may contain about 1.8-2.8% Ag.

Thus, specific embodiments and applications of methods of precipitating highly stable concentrated dispersions of silver nanoparticles have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed.

As used in the description herein and throughout the claims that follow, the meaning of "a," "an," and "the" includes plural reference unless the context clearly dictates otherwise.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

What is claimed is:

1. A method of producing a highly stable concentrated dispersion of silver nanoparticles, comprising the steps of:
   adding a silver compound in deionized water to form a first mixture;
   separately from the steps of adding silver compound in deionized water, dissolving a combination of a reducing dispersant and co-dispersant in deionized water to form a first solution, wherein the co-dispersant is sodium alginate;
   combining the first mixture and the first solution to form a slurry;
   mixing the slurry with a basic solution to form an alkaline basic slurry; and
   heating the alkaline basic slurry to yield highly uniform silver nanoparticles wherein no silver nanoparticle is larger than 25 nm.

2. The method of claim 1, wherein the silver compound comprises silver oxide.

3. The method of claim 1, wherein the reducing dispersant comprises a polysaccharide.

4. The method of claim 3, wherein the reducing dispersant comprises Arabic gum.

5. The method of claim 1, wherein no silver nanoparticle is larger than 15 nm.

6. The method of claim 1, wherein an amount of the silver compound added to the deionized water to form the first mixture is between 1.8-3 times an amount of the combination of the reducing dispersant and co-dispersant dissolved in water.

7. The method of claim 1, wherein the basic solution comprises NaOH.

8. A highly stable concentrated dispersion of silver nanoparticles produced according to the method of claim 1.

9. A method of producing a highly stable concentrated dispersion of silver nanoparticles, comprising the steps of:
   adding a silver compound in deionized water to form a first mixture;
   separately from the steps of adding silver compound in deionized water, dissolving a combination of a reducing dispersant and co-dispersant in deionized water to form a first solution;
   wherein the co-dispersant is sodium alginate,
   combining the first mixture and the first solution to form a slurry;
   mixing the slurry with a basic solution to form an alkaline basic slurry; and
   heating the alkaline basic slurry to yield highly uniform silver nanoparticles wherein no silver nanoparticle is larger than 25 nm, wherein the co-dispersant is present at a concentration of less than 1/8 a concentration of the reducing dispersant.

10. The method of claim 9, wherein the silver compound comprises silver oxide.

11. The method of claim 9, wherein the reducing dispersant comprises a polysaccharide, and wherein the basic solution comprises NaOH.

12. The method of claim 9, wherein no silver nanoparticle is larger than 15 nm.

13. The method of claim 9, wherein an amount of the silver compound added to the deionized water to form the first mixture is between 1.8-3 times an amount of the combination of the reducing dispersant and co-dispersant dissolved in water.

14. A highly stable concentrated dispersion of silver nanoparticles produced according to the method of claim 9.

15. A method of producing a highly stable concentrated dispersion of silver nanoparticles, comprising the steps of:
   adding a silver compound in deionized water to form a first mixture;

separately from the steps of adding silver compound in deionized water, dissolving a combination of a reducing dispersant and co-dispersant in deionized water to form a first solution;

wherein the co-dispersant is sodium alginate, combining the first mixture and the first solution to form a slurry, wherein the volume of the first mixture is between 1.5-2.5 the volume of the first solution;

mixing the slurry with a basic solution to form an alkaline basic slurry; and heating the alkaline basic slurry to yield highly uniform silver nanoparticles wherein no silver nanoparticle is larger than 25 nm.

16. The method of claim 15, wherein the silver compound comprises silver oxide.

17. The method of claim 15, wherein the reducing dispersant comprises a polysaccharide, and wherein the basic solution comprises NaOH.

18. The method of claim 15, wherein no silver nanoparticle is larger than 15 nm.

19. The method of claim 15, wherein an amount of the silver compound added to the deionized water to form the first mixture is between 1.8-3 times an amount of the combination of the reducing dispersant and co-dispersant dissolved in water.

20. A highly stable concentrated dispersion of silver nanoparticles produced according to the method of claim 15.

* * * * *